US00PP36317P3

(12) United States Plant Patent
Kordes

(10) Patent No.: US PP36,317 P3
(45) Date of Patent: Dec. 17, 2024

(54) ROSE PLANT NAMED 'KORhulth 005'

(50) Latin Name: *Rosa hybrida*
Varietal Denomination: KORhulth 005

(71) Applicant: W. KORDES' SÖHNE Rosenschulen GmbH & Co KG, Klein Offenseth-Sparrieshoop (DE)

(72) Inventor: Wilhelm Alexander Kordes, Klein Offenseth-Sparrieshoop (DE)

(73) Assignee: W. KORDES' SÖHNE ROSENSCHULEN GMBH & CO KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 18/442,382

(22) Filed: Feb. 15, 2024

(65) Prior Publication Data

US 2024/0284811 P1 Aug. 22, 2024

(30) Foreign Application Priority Data

Feb. 21, 2023 (QZ) ..... PBR 2023/0453

(51) Int. Cl.
*A01H 5/02* (2018.01)
*A01H 6/74* (2018.01)

(52) U.S. Cl.
USPC ..... Plt./107
CPC ..... *A01H 6/749* (2018.05)

(58) Field of Classification Search
USPC ..... Plt./101, 102, 107
See application file for complete search history.

*Primary Examiner* — Susan McCormick Ewoldt
(74) *Attorney, Agent, or Firm* — Panitch Schwarze Belisario & Nadel LLP; Stephany G. Small; Travis W. Bliss

(57) ABSTRACT

A new and distinct variety of rose plant, referred to by its cultivar name, 'KORhulth 005', is described. The new variety forms in abundance on a substantially continuous basis attractive, peach-colored buds that transitions to pink-colored blossoms with purple blotches. The vegetation is vigorous, and the growth habit is compact spreading. Attractive ornamental foliage is formed.

2 Drawing Sheets

Latin name of genus and species of plant claimed: *Rosa hybrida.*

Variety denomination: 'KORhulth 005'.

CROSS REFERENCE TO RELATED APPLICATIONS

This application claims priority to Plant Breeders' Right Application No. 2023/0453, which was filed at Community Plant Variety Office in the European Union on Feb. 21, 2023, the contents of which are hereby incorporated by reference for all purposes.

STATEMENT REGARDING PRIOR DISCLOSURES BY THE INVENTOR

The first sale or offer for sale of the new variety was May 20, 2022, in Germany. The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of rose plant of the present invention was created by controlled breeding in May 2015, in Offenseth-Sparrieshoop, Germany by artificial pollination wherein two parents were crossed which previously had been studied in the hope that they would contribute the desired characteristics. The female parent (i.e., the seed parent) of the new variety was the 'VEL13kmula' variety (not patented) The male parent (i.e., the pollen parent) of the new variety was the 'CHEWsumstar' variety (not patented).

The parentage of the new variety can be summarized as follows:

'VEL13kmula' x 'CHEWsumstar'

The seeds resulting from the above pollination were sown and small plants were obtained which were physically and biologically different from each other. Selective study resulted in the identification of a single plant of the new variety.

The new variety has been found to undergo asexual propagation at Klein Offenseth-Sparrieshoop, Germany by a number of routes such as vegetative cuttings. Asexual propagation techniques in Klein Offenseth-Sparrieshoop, Germany, such as vegetative cuttings, have shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of rose plant of the present invention possesses the following combination of characteristics:

(a) forms attractive peach-colored buds that transitions to pink-colored blossoms with purple blotches,
(b) exhibits a compact spreading growth habit, and
(c) provides vigorous foliage.

The new variety well meets the needs of the horticultural industry. It can be grown to advantage as attractive ornamentation in parks, gardens, public areas, and residential landscapes. Accordingly, it is particularly well suited for growing in the landscape.

The new variety can be readily distinguished from its ancestors. More specifically, the 'VEL13kmula' variety (i.e., the seed parent) provides a vigorous, climbing growth habit with larger, deep pink-colored blossoms, whereas the new variety provides a compact spreading growth habit and exhibits smaller, pink-colored flowers with purple blotches. Additionally, the new variety provides a compact spreading growth habit, a semi-double flower type and smaller foliage compared to the bushy-upright growth habit, single flower type and larger foliage of the 'CHEWsumstar' variety (i.e., the pollen parent). Moreover, the new variety can be readily distinguished from non-parental related similar varieties. For example, the 'KORatomi' variety (not patented) displays larger, darker green colored leaflets and smaller flowers with 5 petals compared to the leaflets and flowers of the new variety.

The new variety has been named the 'KORhulth 005' variety.

BRIEF DESCRIPTION OF THE PHOTOGRAPHS

The accompanying photographs show, as nearly true as it is reasonably possible to make the same in a color illustration of this character, a typical specimen of the new variety and blossoms of the new variety.

DETAILED BOTANICAL DESCRIPTION

Figure 1:
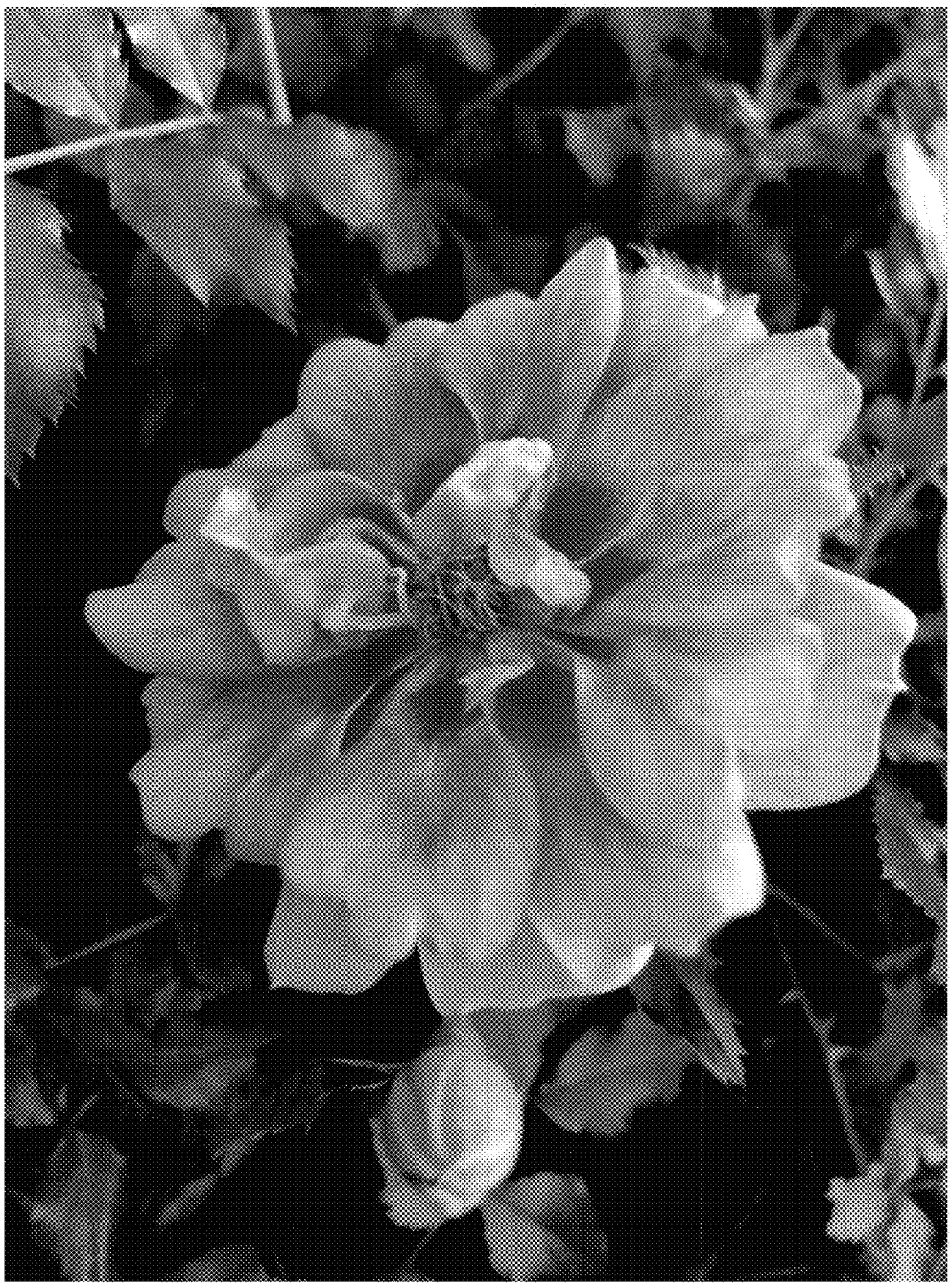
FIG. 1 illustrates a specimen of a fully open flower, close-up view of a plant of the new variety that was approximately three months of age and was grown indoors on its own roots.
Figure 2:
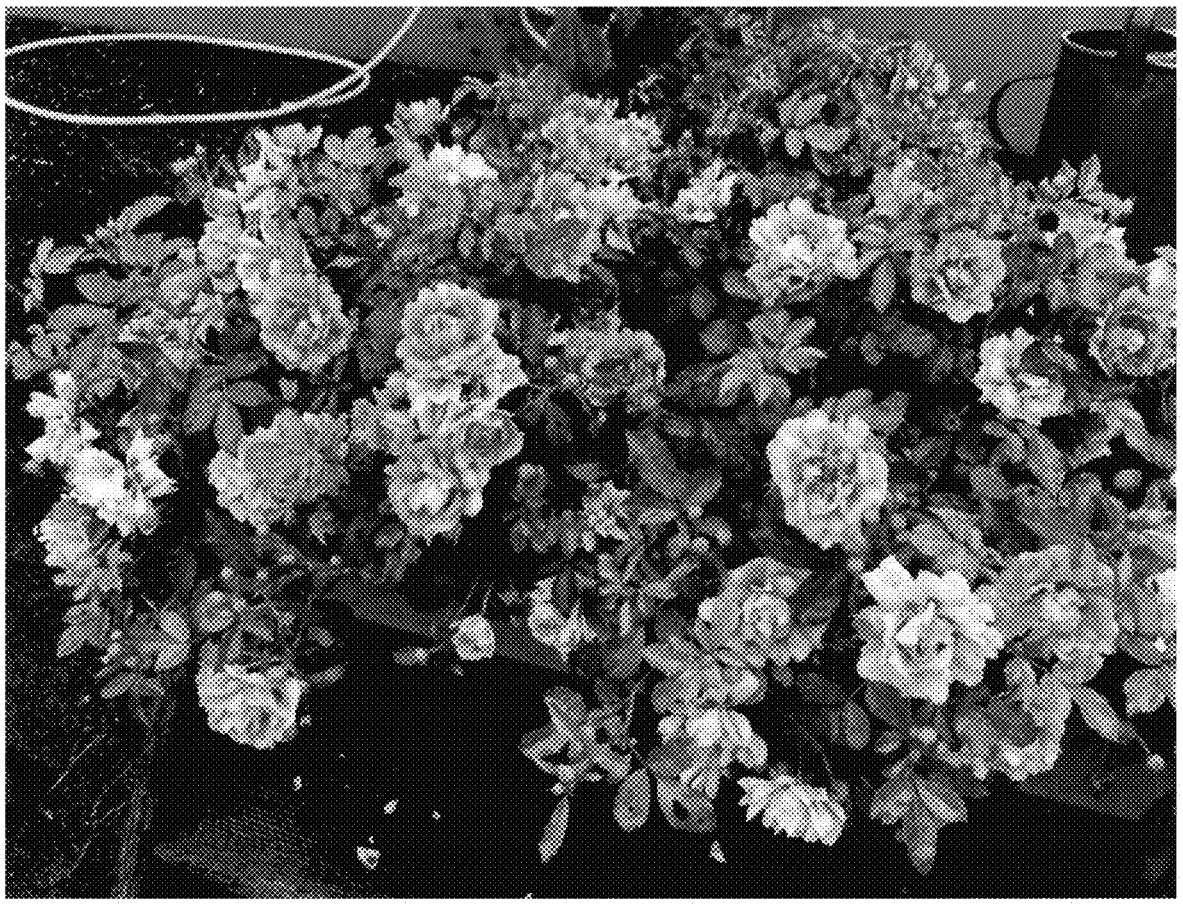
FIG. 2 illustrates a specimen of a plant of the new variety that was approximately six months of age and was grown indoors on its own roots, displaying flowers at varying points of opening.

The chart used in the identification of colors is that of The Royal Horticultural Society (The R.H.S. Colour Chart, 2015 edition). The terminology which precedes reference to the chart has been added to indicate the corresponding color in more common terms and The R.H.S. Colour Chart designation used herein represents the closest color observed on the majority of the specified botanical feature. The illustrated rose plant of the new variety was approximately six months of age and was grown indoors on its own roots.

Botanical classification: *Rosa hybrida* cultivar 'KORhulth 005'.

Commercial classification: Garden Rose.

Plant:

*Habit*.—Compact spreading.

*Height*.—Approximately 70.0 cm on average.

*Width*.—Approximately 50.0 cm on average.

Branches:

*Stem color*.—Old wood is Green Group 143C; young stems are Yellow-Green Group 144C.

*Length*.—Main stems: approximately 25 cm on average. — secondary stems: approximately 10 cm on average.

*Diameter*.—Main stems: typically between 1.0-2.0 mm. — secondary stems: approximately 1.0 mm on average.

*Thorns*.—Young thorns: amount is medium to many; length is approximately 5.0 mm on average; width is typically 1.0-2.0 mm, and color is Yellow Group 4D. — old thorns: amount is medium to many; length is approximately 1.0 cm on average; width is typically 2.0-3.0 mm, and color is Red Group 42C.

*Anthocyanin coloration of young shoots*.—Very minor.

*Internode numbers on entire branch*.—10-12.

*Internode length*.—Typically 2.0-3.0 cm.

Leaflets:

*Number*.—3, 5, and 7.

*Shape*.—Ovate; apex is acuminate; and base is cuneiform.

*Margin*.—Serrate.

*Undulation*.—Weak.

*Glossiness of upper side*.—Very strong glossy.

*Texture*.—Upper surface: smooth. — under surface: smooth.

*Size*.—Terminal leaflet: length is approximately 3.5 cm on average; width is approximately 1.5 cm on average. — lower leaflets: length is typically 2.0 to 2.5 cm; width is typically 1.0 to 1.5 cm. — leaf: length is typically 8.0 to 9.0 cm; width is typically 4.0 to 5.0 cm.

Foliage:

*Young foliage*.—Upper surface color: Green Group 143B. — under surface color: Green Group 139C.

*Old foliage*.—Upper surface color: Green Group 139 A. — under surface color: Green Group 138B.

*Venation*.—Pattern is fine branched and color is indistinguishable from foliage color.

*Petiole*.—Texture: upper surface is smooth; under surface is smooth. — length: approximately 5 mm on average. — width: typically 0.3 to 0.5 mm on average. — upper surface color: Green Group 141B. — under surface color: Green Group 141B.

*Rachis*.—Length: typically 0.8 to 1.0 cm on average. — width: typically 0.2 to 0.3 mm on average. — upper surface color: Green Group 141B. — under surface color: Green Group 141B.

*Stipules*.—Size: very small, almost absent. — upper surface color: Green Group 141B. — lower surface color: Green Group 141B.

Inflorescence:

*Number of flowers*.—About 16-20 blooms on average on a plant at once.

*Number of blossoms per stem or in a cluster*.—Typically 5-7 blooms per cluster.

*Peduncle*.—Color: Green Group 141C. — diameter: typically 2.0 to 3.0 mm. — length: typically 2.0 to 3.0 cm. — surface texture: slightly prickled.

*Sepals*.—Number 5. — upper surface color and texture: Green Group 143B; fluffy. — under surface color and texture: Green Group 142B; fluffy. — size: length is typically 0.5 to 0.7 cm; width is approximately 0.3 cm on average. — margin: smooth (even). — shape: pointed ovate. — extensions: absent or very weak.

*Buds*.—Color (when opening): Red Group 37B. — size: length is approximately 1.0 cm on average; diameter is typically 0.5 to 0.7 cm.

*Flower*.—Form: semi-double. — type: cluster flowered. — profile: cuplike. — shape when viewed from top: irregular rounded. — diameter: approximately 5.0 to 6.0 cm on average. — depth: typically 4.0 to 5.0 cm. — petal color when opening: Red Group 37B; basal spot is medium sized and Red-Purple Group 57B. — petal color of medium opened flower: Red-Purple Group 68B on the base to 68D on the tip. — petal color when fully opened: the upper surface is Red-Purple Group 73B towards the base and changes to Red-Purple Group 73D toward the tip; with a medium basal spot of Red-Purple Group 67A; the under surface is Red-Purple Group 69A towards the base to 69C toward the tip.

*Fragrance*.—Medium, spicy.

*Petal*.—Number: typically about 35-40. — drop: drop cleanly. — length: typically 1.5 to 2.0 cm. — width: typically 1.0 to 1.5 cm. — overall shape: ovoid. — margin: heart shaped. — reflex: moderate.

*Petaloids*.—Number: typically 4-5. — length: approximately 1.0 cm on average. — width: approximately 0.5 cm on average. — color: upper and under surfaces are a color between Red-Purple Group 73A and 73B.

*Stamen*.—Number: typically 30-35. — anthers: color is Yellow-Orange Group 22B; length is approximately 0.5 mm on average; width is approximately 0.3 mm; and shape is oval. — filaments: length is typically 2.0 to 3.0 mm and color is Yellow-Orange Group 22A.

*Pistils*.—Number: typically 12-15. — style: length is typically less than 1.0 mm and color Yellow Group 3D. — stigma: length is typically 2.0 to 3.0 mm; width is approximately 0.005 mm; shape is fan shaped; color is Yellow Group 3D.

*Receptacle*.—Diameter: typically 0.2 to 0.3. — length: approximately 0.5 cm on average. — shape: urn shaped. — color: Green Group 143A. — surface texture: smooth.

*Pollen*.—Very little, color is Yellow-Orange Group 23A.

*Hips/seed*.—Absent.

Development:

*Vegetation*.—Moderate vigorous.

*Blossoming*.—Continuous from June to September or October in North Germany.

*Disease resistance*.—Good resistance for powdery mildew (*Sphaerotheca pannosa*) and rust (*Phragmidium* sp.).

*Hardiness*.—Hardy to USDA Zone 6.

The new 'KORhulth 005' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of rose plant named 'KORhulth 005' characterized by the following combination of characteristics:

(a) forms attractive peach-colored buds that transitions to pink-colored blossoms with purple blotches, (b) exhibits a compact spreading growth habit, and (c) provides vigorous foliage;

substantially as herein shown and described.

* * * * *